United States Patent [19]

Messori et al.

[11] 4,230,853

[45] Oct. 28, 1980

[54] PROCESS FOR PREPARING CHLORO-BIS(ALKYLAMINO)-s-TRIAZINES

[75] Inventors: Vittorio Messori; Renato Francese, both of Turin, Italy

[73] Assignee: Rumianca S.p.A., Turin, Italy

[21] Appl. No.: 80,720

[22] Filed: Oct. 1, 1979

[30] Foreign Application Priority Data

Sep. 29, 1978 [IT] Italy .............................. 28219 A/78

[51] Int. Cl.³ .......................................... C07D 251/50
[52] U.S. Cl. ..................................................... 544/204
[58] Field of Search ......................................... 544/204

[56] References Cited

U.S. PATENT DOCUMENTS

| | | | |
|---|---|---|---|
| 3,436,394 | 4/1969 | Saul ..................................... | 544/204 |
| 3,590,040 | 6/1971 | Ferguson et al. .................... | 544/204 |
| 3,639,399 | 2/1972 | Daugherty et al. .................. | 544/204 |
| 3,681,335 | 8/1972 | Saul et al. ........................... | 544/204 |
| 3,681,337 | 8/1972 | Petree ................................. | 544/204 |
| 4,054,739 | 10/1977 | Haschke et al. ..................... | 544/204 |
| 4,058,662 | 10/1977 | Haschke et al. ..................... | 544/204 |
| 4,099,006 | 7/1978 | Baldi et al. .......................... | 544/204 |
| 4,182,874 | 1/1980 | Baldi ................................... | 544/204 |

*Primary Examiner*—John M. Ford
*Attorney, Agent, or Firm*—Sughrue, Rothwell, Mion, Zinn and Macpeak

[57] ABSTRACT

In the commercial process for preparing chloro-bis(alkylamino)-s-triazines by step-wise replacement of two chlorine atoms of cyanuric chloride by means of alkylamino groups in which a molar excess of alkylamine is used in the second replacement step, the formation of tris(alkylamino)-s-triazines is suppressed by adding to the reaction mixture, after the second chlorine atom has been replaced with an alkylamino group, an oxidizing agent selected from the group consisting of hydrogen peroxide and alkali metal hypochlorites, persulphates and permanganates, in an amount of at least 1 equivalent for every mole of unreacted alkylamine present in the said reaction mixture.

11 Claims, No Drawings

PROCESS FOR PREPARING CHLORO-BIS(ALKYLAMINO)-s-TRIAZINES

The present invention relates to the preparation of chloro-bis(alkylamino)-s-triazines by means of a process which allows the elimination, or at least the substantial reduction, of the formation of tris(alkylamino)-s-triazines.

The chloro-bis(alkylamino)-s-triazines are compounds definable by means of the general formula:

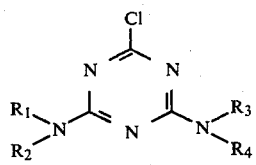

where $R_1$, $R_2$, $R_3$ and $R_4$ independently are hydrogen, an alkyl radical containing from 1 to 5 atoms of carbon, or particular groups of a different nature from the alkyl group.

The chloro-bis(alkylamino)-s-triazines are valued herbicides and the compounds most known belonging to this group are: 2-chloro-4-ethylamino-6-isopropylamino-s-triazine (atrazine), 2-chloro-4,6-bis(ethylamino)-s-triazine (simazine) and 2-chloro-4,6-bis-(isopropylamino)-s-triazine (propazine). The herbicidal characteristics of these compounds are described in U.S. Pat. No. 2,891,855 here given as a reference.

The chloro-bis(alkylamino)-s-triazines are generally prepared from cyanuric chloride by step-wise replacement of two atoms of chlorine, as reported, for example, by W. Pearlman and C. K. Banks in J.Am.Chem.Soc. 70, 3726 (1948). In practice the reaction is carried out according to the general scheme:

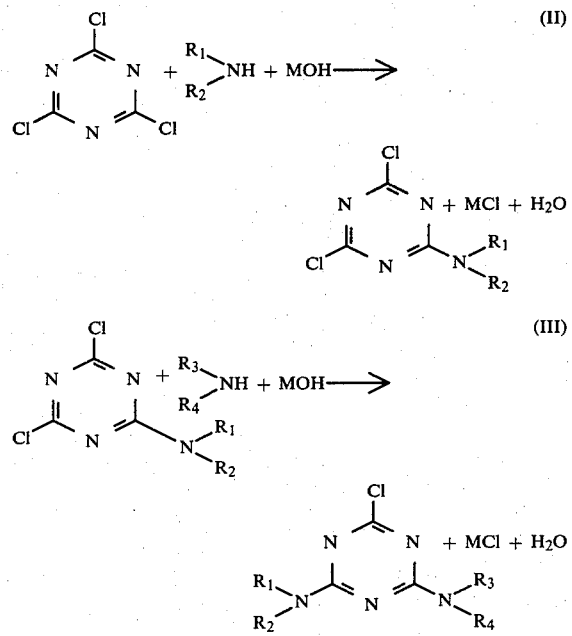

where M represents an alkali metal.

In particular the preparation of atrazine is generally carried out by a discontinuous method, by reacting, in a first reaction stage, cyanuric chloride with isopropylamine in the presence of sodium hydroxide to give 2,4-dichloro-6-isopropylamino-s-triazine. This latter is reacted, in a second stage, with ethylamine and with a further quantity of sodium hydroxide with the subsequent formation of the desired product: 2-chloro-4-ethylamino-6-isopropylamino-s-triazine.

The reactions described may be carried out in an aqueous medium or in an organic medium. Generally it is preferred to conduct the reactions in a water-organic compound medium, using as an organic compound a solvent for cyanuric chloride which is insoluble in water, or is partially or totally soluble in the same, i.e., two-phase or single-phase water-organic compound systems.

Generally the reaction (II) given above is carried out by using stoichiometric quantities of the reagents, while the reaction (III) is carried out with a quantity of alkylamine and of sodium hydroxide greater than those needed for the production of chloro-bis(alkylamino)-s-triazine. This method of operation is justified by the need to completely convert the 2,4-dichloro-6-alkylamino-s-triazine in view of the undesirable characteristics of such compounds. Thus, for example, 2,4-dichloro-6-isopropylamino-s-triazine has skin-irritant properties to such an extent that it must not be present in the final product in quantities greater than about 0.5% by weight.

On the other hand the used of excess alkylamine results in disadvantages due to the formation of tris(alkylamino)-s-triazine, by reaction of the excess alkylamine with the chloro-bis(alkylamino)-s-triazine. For example, the reaction of ethylamine with 2-chloro-4-ethylamino-6-isopropylamino-s-triazine results in the formation of 2,4-bis(ethylamino)-6-isopropylamino-s-triazine. This latter compound is undesirable in that it renders the recovery of atrazine from the reaction products difficult, hinders the grinding of the dried atrazine and reduces the stability and flowability of the liquid formulations containing atrazine. Probably these undesirable effects are caused, at least in part, by the 2,4-bis-(ethylamino)-6-isopropylamino-s-triazine, which is a tacky solid of low melting point and waxy appearance. This by-product mainly forms in the stage of recovery of the reaction products, especially in the stage of distillation of the organic solvent used in the reaction medium, rather than during the reaction (III) described above.

Therefore, various expedients have been proposed in the art to separate, or at least to render to some extent non-active, the unreacted alkylamine at the end of the reaction (III) and in particular to separate or to deactivate, the ethylamine in the case of the preparation of atrazine.

Thus, for example, according to U.S. Pat. No. 3,681,335 on completion of the formation of the chloro-bis(alkylamino)-s-triazine, a strong acid is added to the reaction medium to bring the pH from 11.5–12 to values of the order of 5–9 (preferably of the order of 6.5–7.5). In this manner the alkylamine is deactivated and the distillation of the organic solvent may be carried out without danger of formation of tris(alkylamino)-s-triazine. According to the patent under discussion, the pH is brought back to values of the order of 11–12.5 in the residual suspension from the distillation containing the chloro-bis(alkylamino)-s-triazine before the separation of the latter is carried our by means of filtration. The characteristics of filterability are thus improved.

Moreover, according to U.S. Pat. No. 3,681,337, immediately after the end of reaction (III), cyanuric chloride is added to the reaction mixture in such amounts as to neutralize the free amine and form the dichloroalkylamino-s-triazine, which is then hydrolyzed together with the free cyanuric chloride. Since the hydrolysis products are soluble in water their removal becomes easy.

Finally, according to U.S. Pat. No. 3,705,156 formaldehyde is added to the products of the reaction (III), in order to induce the formation of condensation products between formaldehyde and the free alkylamine. These condensation products are removed during the distillation and the subsequent filtration.

The known processes for the suppression of the formation of tris(alkylamino)-s-triazines have disadvantages due, essentially, to their complexity; thus, for example, in the case of U.S. Pat. No. 3,681,335 the pH has to be adjusted twice and in the case of U.S. Pat. No. 3,681,337 the excess alkylamine is reacted with added cyanuric chloride and the unreacted cyanuric chloride together with the dichloro-alkylamino-s-triazine formed are subsequently hydrolysed. Moreover, the reactions provided in the latter patent and in U.S. Pat. No. 3,705,156 result in the formation of new molecular species of a complex nature which renders their separation from the final desired product problematical and results in the pollution of this desired product with various chemical compounds.

The object of the present invention is, therefore, to overcome these disadvantages of the known processes for the preparation of chloro-bis(alkylamino)-s-triazines free, or substantially free, of tris(alkylamino)-s-triazine.

The present invention provides a process for preparing chloro-bis(alkylamino)-s-triazine by step-wise replacement of two chlorine atoms of cyanuric chloride by means of alkylamino groups in an alkaline medium comprising water and a liquid organic compound which is a solvent for cyanuric chloride, in which a molar excess of alkylamine is used in the second replacement step, characterized in that the formation of tris(alkylamino)-s-triazine is suppressed by adding to the reaction mixture, after the second chlorine atom has been replaced with an alkylamino group, an oxidizing agent selected from the group consisting of hydrogen peroxide and alkali metal hypochlorites, persulphates and permanganates, in an amount of at least 1 equivalent for every mole of unreacted alkylamine present in the said reaction mixture.

The treatment with the oxidizing agent may be carried out at a temperature of from 20° to 100° C., and preferably from 20° to 70° C., usually for a time of from 0.5 to 10 minutes and preferably of the order of 1–2 minutes. The treatment is conveniently carried out under stirring. Of the hypochlorites, persulphates and permanganates, the sodium and potassium salts are preferred. The best results are generally achieved with sodium and potassium hypochlorites, followed, in order, by hydrogen peroxide and sodium and potassium persulphates. Sodium and potassium permanganates generally produce inferior results, even though they may be used with advantage in the process of the invention.

As has been stated above, the oxidizing agents are used in an amount of at least one equivalent for every mole of unreacted alkylamine present in the reaction mixture at the end of the reaction (III). The upper limit for these oxidizing agents is not particularly critical and depends essentially on economic considerations. In any case, it is not convenient to exceed values of 2.5 equivalents per mole of alkylamine, the best results being generally obtained with amounts of oxidizing agent of the order of 1.5–2 equivalents.

Surprisingly, the oxidizing agents mentioned above are highly selective in their action towards the free alkylamine in that they do not affect the other constituents of the reaction medium to an analytically determinable extent. It should be noted, in this respect, that any unreacted oxidizing agents left after the treatment in question may remain in the reaction medium for relatively long periods of time without danger to the useful constituents.

The molar excess of alkylamine used in the substitution of the second chlorine atom of cyanuric chloride is generally from 1 to 6%, and preferably of the order of 3%. With this excess it is, in fact, possible to convert all, or substantially all, the 2,4-dichloro-6-alkylamino-s-triazine. It is thought that, when operating according to the process of the invention, the free alkylamine is converted into oxidation products by contact with the oxidizing agent, thus preventing its reaction with the chloro-bis(alkylamino)-s-triazine. It is thus possible to distill off the solvent and to recover from the distillation residue a chloro-bis(alkylamino)-s-triazine free from tris(alkylamino)-s-triazine, or at least having a content of the latter of less than about 0.05% by weight. Hence the treatment with the oxidizing agent constitutes an extremely efficient method for obtaining chloro-bis(alkylamino)-s-triazines with high purity.

Moreover, since the oxidizing agent is soluble in water and any excess is removed together with the oxidizing product of the alkylamine during the conventional filtration and washing of the chloro-bis(alkylamino)-s-triazine, the process of the present invention is simple and convenient.

The chloro-bis(alkylamino)-s-triazines obtained according to the present invention are useful in herbicidal formulations (both as wettable powders and as liquid suspensions) which are characterised by a great facility of use and by an increased herbicidal efficiency. These formulations do not have any of those known disadvantages resulting from the presence of tris(alkylamino)-s-triazines in their storage or their use.

By means of the process of the present invention there may be prepared all the compounds definable by means of the general formula (I), in which $R_1$, $R_2$, $R_3$ and $R_4$ independently are hydrogen, alkyl radicals either the same or different, having from 1 to 5 atoms of carbon, or other particular groups different from alkyl groups. Examples of alkyl radicals are: methyl, ethyl, isopropyl, cyclopropyl, n-butyl, sec-butyl and tert-butyl.

In the description which follows, specific reference will be made to the preparation of 2-chloro-4-ethylamino-6-isopropylamino-s-triazine. This is for reasons of simplicity, it being taken into account that wholly similar considerations are valid for the other chloro-bis(alkylamino)-s-triazines.

(a) PREPARATION OF 2,4-DICHLORO-6-ISOPROPYLAMINO-S-TRIAZINE

In stage (a) cyanuric chloride, isopropylamine and sodium hydroxide are reacted to produce 2,4-dichloro-6-isopropylamino-s-triazine according to the following scheme:

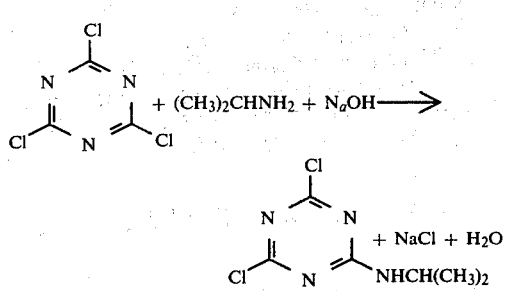

(IV)

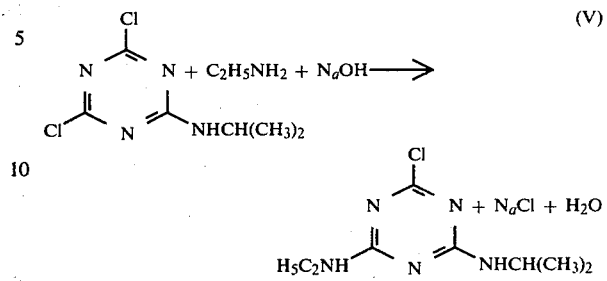

(V)

The quantities of isopropylamine and of sodium hydroxide are equivalent, or nearly equivalent, to those needed for the formation of the 2,4-dichloro-6-isopropylamino-s-triazine. In place of sodium hydroxide there may be used sodium carbonate, of the hydroxide or carbonate of other alkali metals, such as lithium and potassium.

The reaction is carried out in the presence of an organic compound, inert under the reaction conditions and having a good solvating power towards cyanuric chloride. Organic solvents suitable for the purpose are: diethyl ether, dioxan, diethyl Cellosolve, benzene, toluene, xylene, chlorobenzene, acetone, methyl ethyl ketone, carbon tetrachloride or such other organic solvents known in the art in respect of the preparation of chloro-bis(alkylamino)-s-triazines. These solvents are preferably used in mixture with water, in the form of a single-phase system, such as water-acetone and water-dioxan, or a two-phase system, such as water-benzene and water-chlorobenzene. As a rule the cyanuric chloride is fed in in the form of a solution in the chosen organic solvent, while the inorganic base and the alkylamine are fed in in the form of an aqueous solution. In the choice of the solvent it is also necessary to take account of its separability, by means of distillation, from the 2-chloro-4-ethylamino-6-isopropylamino-s-triazine finally produced. The quantities of organic solvent and of water used are not particularly critical; it is however convenient to maintain the weight ratios between the two at values of from 3:1 to 3:2. Moreover, good results are obtained by regulating the feeds such that the concentration of the 2,4-dichloro-6-isopropylamino-s-triazine at the end of stage (a) is from 10 to 20% by weight with respect to the weight of the chosen organic solvent.

The temperature is generally kept at a value of from $-5°$ to $60°$ C. Overpressure is not generally applied, or the overpressure necessary to maintain the reaction medium in the liquid phase is applied.

The 2,4-dichloro-6-isopropylamino-s-triazine may be prepared by using a continuous or a discontinuous process. In the second case the sodium hydroxide and the isopropylamine are generally added in the form of aqueous solutions to the cyanuric chloride dissolved in the chosen organic solvent.

At the end of stage (a) it is possible to carry out a separation of materials from the reaction mixture, such as the aqueous phase, or the reaction mixture may be conveyed directly to the following reaction stage.

(b) PREPARATION OF 2-CHLORO-4-ETHYLAMINO-6-ISO-PROPYLAMINO-S-TRIAZINE

In stage (b) the 2,4-dichloro-6-isopropylamino-s-triazine obtained in stage (a), ethylamine and sodium hydroxide, are reacted to produce 2-chloro-4-ethylamino-6-isopropylamino-s-triazine according to the scheme:

The ethylamine and sodium hydroxide are generally used in a molar excess of from 1% to 6%. Usually this excess is maintained at values of the order of 3%. The ethylamine and the sodium hydroxide are conveniently fed in in the form of an aqueous solution.

The reaction is conveniently carried out at a temperature of from 25° to 90° C. and for a period such as to completely convert the 2,4-dichloro-6-isopropylamino-s-triazine, or at least to convert more than 99.5% of this compound.

The other operating conditions for stage (b) are entirely similar to those described for stage (a).

(c) TREATMENT WITH THE OXIDIZING AGENTS AND SEPARATION OF THE REACTION PRODUCTS

A substance having an oxidizing action on ethylamine is added to the reaction mixture coming from stage (b). This addition is conveniently carried out within five to ten minutes from the end of stage (b) and before the distillation of the organic solvent. The oxidizing substances suitable for the purpose are those indicated above: it is convenient to feed these into the reaction mixture in the form of aqueous solutions. The oxidation of the ethylamine occurs rapidly and it suffices to maintain the mass under agitation for a few minutes (1–2 minutes). The operating temperature is not particularly critical. Thus the solution of oxidizing agent may be fed in at the temperature at which the reaction mixture is discharged from stage (b), but it is also possible to carry out the reaction within a wide range of temperatures such as from 20° to 100° C.

The distillation of the organic solvent is then carried out at a pressure equal to or less than atmospheric. The distillation residue generally consists of a dense suspension of the 2-chloro-4-ethylamino-6-isopropylamino-s-triazine and also contains the products resulting from the oxidation of the ethylamine together with possible residual oxidizing agents in a dissolved form. This suspension is filtered and washed and the atrazine is then recovered by known methods.

The atrazine, or, in general, any other compound of the general formula (I) prepared by the above method, typically contains less than 0.05% by weight of tris(alkylamino)-s-triazine.

EXAMPLE 1

A reactor of 20 liter capacity, provided with an agitator, a thermometer and two separate apertures for the feed of the reagents, is used. The reactor is furnished with means for its cooling. Into the reactor is loaded initially a solution of about 1840 g (10 moles) of cyanuric chloride in about 5000 g of toluene (boiling point 110.6° C.). Hardly has the temperature of the solution stabilised at 5° C. than there are simultaneously added, under strong agitation, 840 g of an aqueous solution containing 70% by weight of isopropylamine (10 moles) and 1340 g of an aqueous solution containing 30% by weight of sodium hydroxide (10 moles). The two feed rates are controlled so that the addition of the isopropylamine solution finishes in 25 minutes and that of the sodium hydroxide in 28 minutes.

During the addition, the temperature rises from 5° C. up to 20°-22° C., while the pH, from an initial value of 2-3, rises to a maximum value of 9.5 then to fall to 6-7.

After the addition, the mixture is maintained for 10 minutes at 20° C., and 2000 g of dilute hydrochloric acid (0.1% by weight) are introduced so as to bring the pH of the medium to a value of about 2-3. The mixture is agitated for 15 minutes and then decanted and the aqueous layer is separated.

To the solution of 2,4-dichloro-6-isopropylamino-s-triazine in toluene remaining in the reactor are added, under strong agitation, about 915 g of an aqueous solution containing 50% by weight of ethylamine (10.15 moles) and about 1353 g of an aqueous solution containing 30% by weight of sodium hydroxide (10.15 moles). The said solutions are added in the same manner as in the first reaction step. During the second addition the temperature rises from 25° to 50° C. and the final pH is equal to 11-12. The dense suspension thus obtained is divided into two parts as quickly as possible. One part (A) is submitted to distillation to remove the toluene in the form of an azeotropic toluene-water mixture, by operating at 85°-100° C. To the distillation residue are added 3,700 ml of water and the suspension thus obtained is filtered at 60° C. The filtered solid is washed until the sodium chloride has been removed completely. After drying for ten hours in an oven at 100° C., 2-chloro-4-ethylamino-6-isopropylamino-s-triazine is obtained with a yield of the order of 96%.

The other part (B) is admixed with an aqueous solution of sodium hypochlorite. The quantity of the latter is given in Table 1 as the number of equivalents for each mole of free ethylamine.

The suspension thus obtained is agitated for two minutes at 50° C. The sample (B) is then submitted to the treatments of distillation and recovery of atrazine from the distillation residue, by operating under the same conditions as in the case of sample (A).

The product obtained from sample (B) consists of atrazine with a purity of about 99%.

Suspensions are prepared from the products obtained from samples (A) and (B) with a concentration of 45% by dispersing the finely ground atrazine in a liquid medium consisting of water, wetting agents, dispersing agents and suspending agents. The fluidity of the formulate is determined immediately after the formulation and after one month and six months of storage under ambient conditions. The results are summarized in Table I.

EXAMPLES 2 AND 3

Two runs are carried out as in Example 1 using respectively 3% and 6% molar excess of ethylamine with respect to the stoichiometric value. The quantity of sodium hypochlorite added is given in Table I as the number of equivalents for every mole of free ethylamine at the end of stage (b).

The results are summarised in Table I. The content of 2,4-bis(ethylamino)-6-isopropylamino-s-triazine in the products obtained from the samples (B) is in every case less than the quantity which can be determined analytically.

TABLE I

| Ex. | Sample | Molar Excess EtNH$_2$ | NaClO equivalents | fluidity initial | after 1 month | after 6 months |
|---|---|---|---|---|---|---|
| 1 | A | 1.5 | — | fluid | dense | — |
| 1 | B | 1.5 | 2 | fluid | fluid | fluid |
| 2 | A | 3.0 | ' | fluid | dense | — |
| 2 | B | 3.0 | 1.5 | fluid | fluid | fluid |
| 3 | A | 6.0 | — | fluid | dense | — |
| 3 | B | 6.0 | 1 | fluid | fluid | fluid |

We claim:

1. In a process for preparing chloro-bis(alkylamino)-s-triazine by step-wise replacement of two chlorine atoms of cyanuric chloride by means of alkylamino groups in an alkaline medium comprising water and a liquid organic compound which is a solvent for cyanuric chloride, in which a molar excess of alkylamine is used in the second replacement step, the method of suppressing the formation of tris(alkylamino)-s-triazines which comprises adding to the reaction mixture, after the second chlorine atom has been replaced with an alkylamino group, an oxidizing agent selected from the group consisting of hydrogen peroxide and alkali metal hypochlorites, persulphates and permanganates, in an amount of at least 1 equivalent for every mole of unreacted alkylamine present in the said reaction mixture.

2. The process of claim 1, wherein the oxidizing agent is added in an amount of from 1 to 2.5 equivalents for every mole of unreacted alkylamine.

3. The process of claim 1, wherein the oxidizing agent is added in an amount of from 1.5 to 2 equivalents for every mole of unreacted alkylamine.

4. The process of claim 1, wherein said alkali metal is sodium.

5. The process of claim 1, wherein said alkali metal is potassium.

6. The process of claim 1, wherein said oxidizing agent is added within a period of 10 minutes from the completion of the second replacement step.

7. The process of claim 1, wherein the mass resulting from the addition of the oxidizing agent to the reaction mixture is stirred for a period of from 0.5 to 10 minutes at a temperature of from 20° to 100° C.

8. The process of claim 1, wherein said molar excess of alkylamine is from 1 to 6%.

9. The process of claim 1, wherein a chloro-bis(alkylamino)-s-triazine is produced with a content of tris-alkylamino-s-triazine of less than 0.05% by weight.

10. The process of claim 1, wherein 2-chloro-4-ethylamino-6-isopropylamino-s-triazine is produced with a content of 2-4-bis(ethylamino)-6-isopropylamino-s-triazine of less than 0.05% by weight.

11. The process of claim 1, wherein said oxidizing agent is sodium hypochlorite.

* * * * *